United States Patent [19]

Adair

[11] Patent Number: 5,284,474
[45] Date of Patent: Feb. 8, 1994

[54] TROCHAR SYSTEM FOR LAPAROSCOPY

[76] Inventor: Edwin L. Adair, 99 Inverness Dr. East, Englewood, Colo. 80112

[21] Appl. No.: 954,655

[22] Filed: Sep. 30, 1992

Related U.S. Application Data

[63] Continuation of Ser. No. 896,461, Jun. 8, 1992, which is a continuation of Ser. No. 625,413, Dec. 11, 1990.

[51] Int. Cl.⁵ ............................................ A61M 5/178
[52] U.S. Cl. ..................................... 604/164; 606/185; 606/172
[58] Field of Search ................. 604/51, 158, 164–171, 604/96, 272, 273, 274; 606/185; 128/753, 754

[56] References Cited

U.S. PATENT DOCUMENTS

| | | | |
|---|---|---|---|
| 958,854 | 5/1910 | Bunn | 604/267 |
| 1,527,291 | 2/1925 | Zorraquin | |
| 2,630,803 | 3/1953 | Baran | 128/221 |
| 3,709,211 | 1/1973 | Hawkins | 604/267 |
| 3,840,008 | 10/1974 | Noiles | 128/221 |
| 3,853,127 | 12/1974 | Spademan | 604/167 |
| 3,952,742 | 4/1976 | Taylor | 604/164 |
| 3,982,533 | 9/1976 | Wiest | 128/184 |
| 4,096,860 | 6/1978 | McLaughlin | 128/214.4 |
| 4,230,123 | 10/1980 | Hawkins, Jr. | 604/165 |
| 4,424,833 | 1/1984 | Spector et al. | 137/849 |
| 4,473,067 | 9/1984 | Schift | 604/167 |
| 4,535,773 | 8/1985 | Yoon | 604/51 |
| 4,685,901 | 8/1987 | Parks | 604/96 |
| 4,769,018 | 9/1988 | Wilson | 604/283 |
| 4,786,281 | 11/1988 | Valentini et al. | 604/167 |
| 4,808,168 | 2/1989 | Warring | 604/158 |
| 4,869,717 | 9/1989 | Adair | 604/51 |
| 4,966,588 | 10/1990 | Rayman et al. | 604/165 |
| 5,030,206 | 7/1991 | Lander | 604/164 |

FOREIGN PATENT DOCUMENTS 2308346 11/1976 France .

OTHER PUBLICATIONS

Picture of Veress needle apparatus.

*Primary Examiner*—C. Fred Rosenbaum
*Assistant Examiner*—Manuel Mendez
*Attorney, Agent, or Firm*—Fields, Lewis, Pittenger & Rost

[57] ABSTRACT

In accordance with this invention a disposable trochar for use as a gas insufflation needle is provided for insertion through the abdominal wall of a patient and into a body cavity. It has an outer sheath with a tubular body, a distal open end and a proximate open end. The distal end may have means which is expandable after the trochar has been inserted into the body cavity to minimize dislocation of the outer sheath during use. A cannula is removably received within in the sheath which has a sharp distal end extendable beyond the distal end of the sheath and an enlarged head at the proximate end of the cannula. The head has a flat land which is engageable with the proximate end of the sheath to limit the extension of the distal end of the cannula beyond the distal end of the sheath. A rod is mounted within the cannula for longitudinal movement between a retracted position and an extended position. A blunt member is provided at the distal end of the rod extending beyond the sharp distal end of the cannula when in extended position. A spring, in a cavity in the head, is attached to the proximate end of the rod urging it toward the extended position. The method of using the trochar is also disclosed.

7 Claims, 3 Drawing Sheets

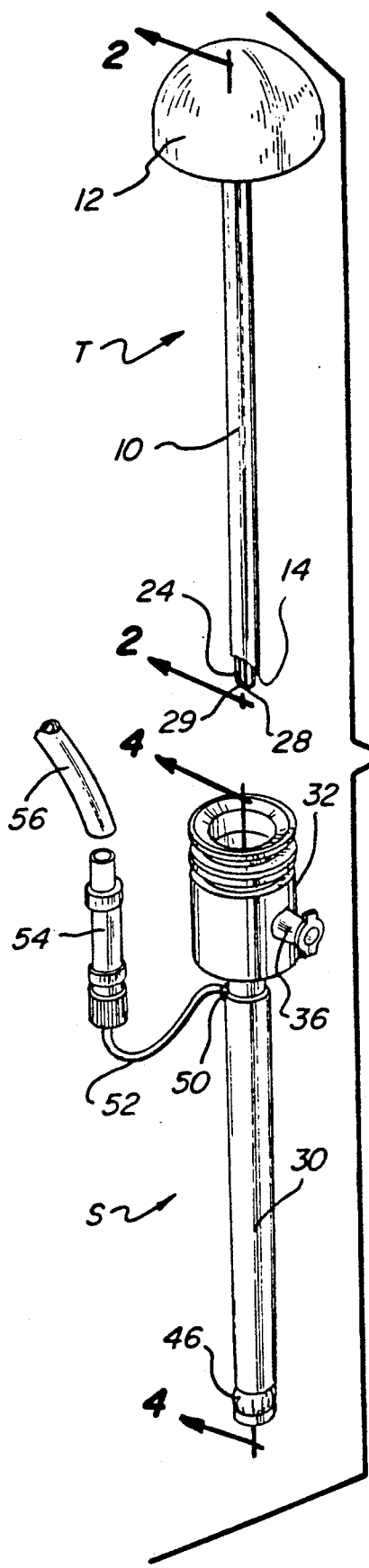
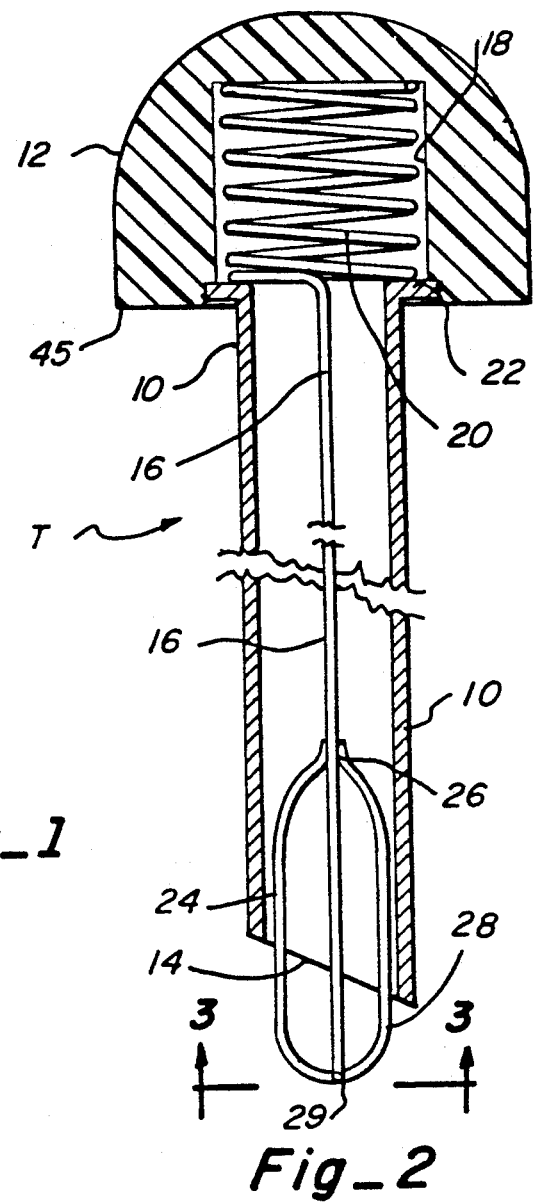
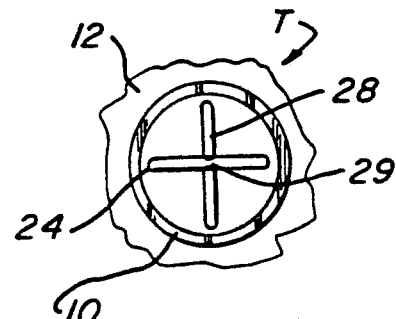

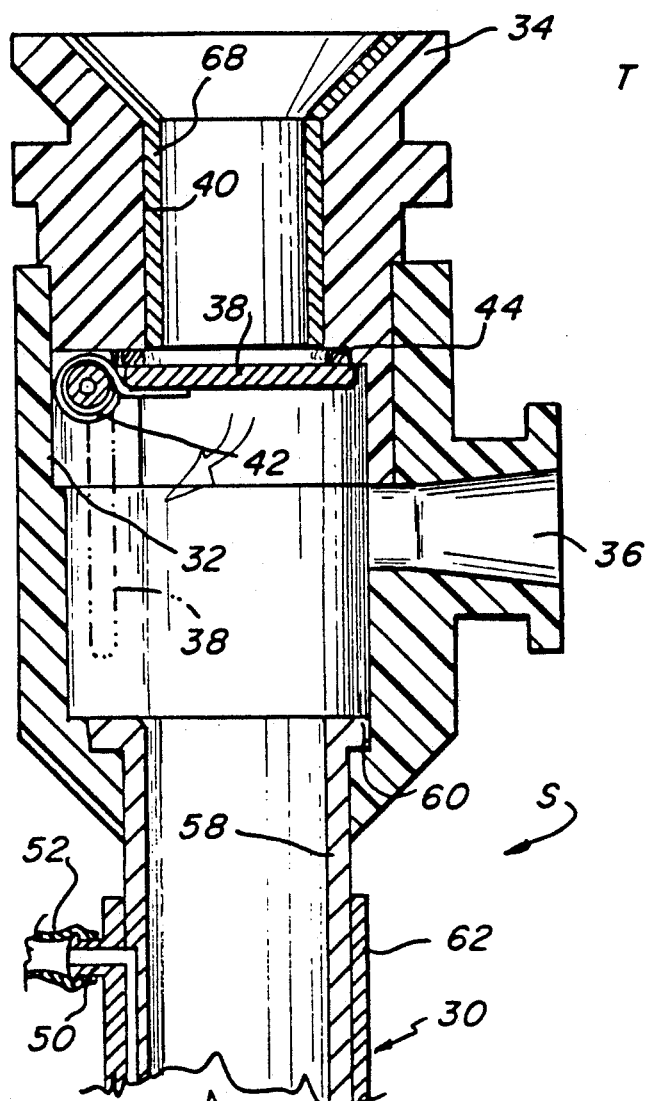
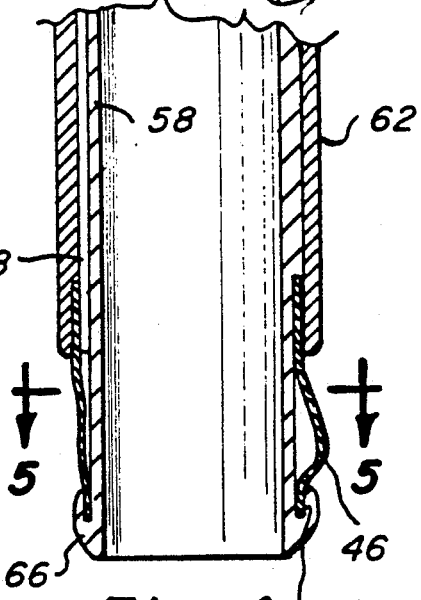
Fig_4
Fig_5
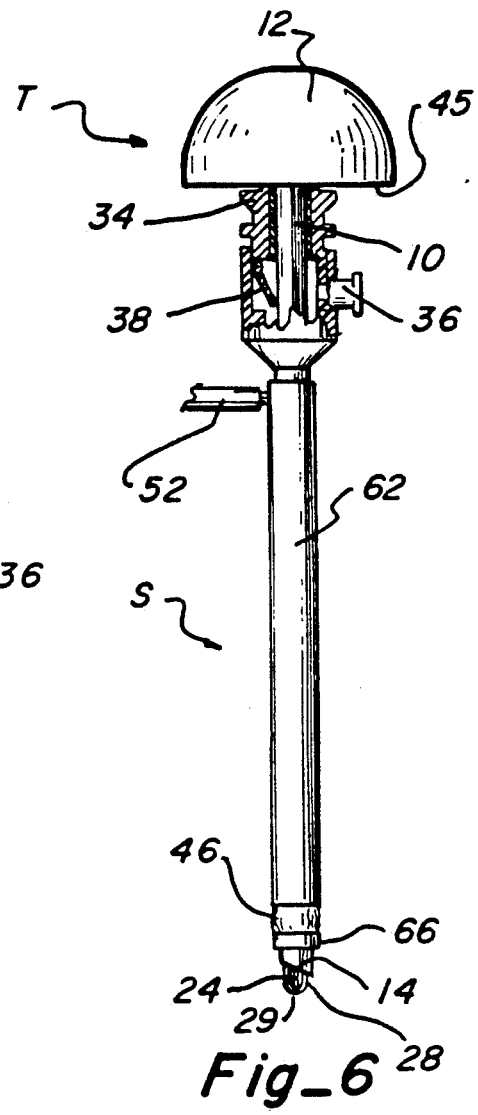
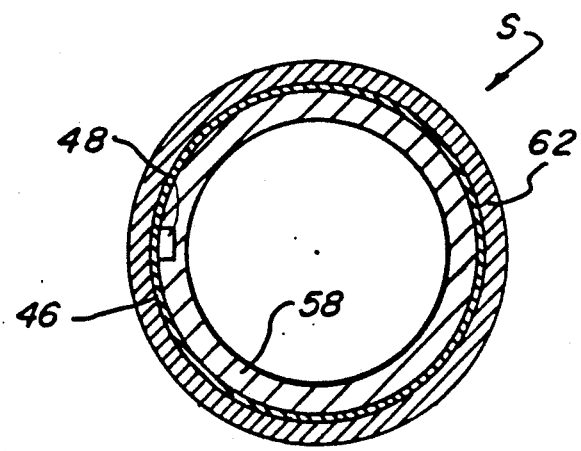
Fig_6

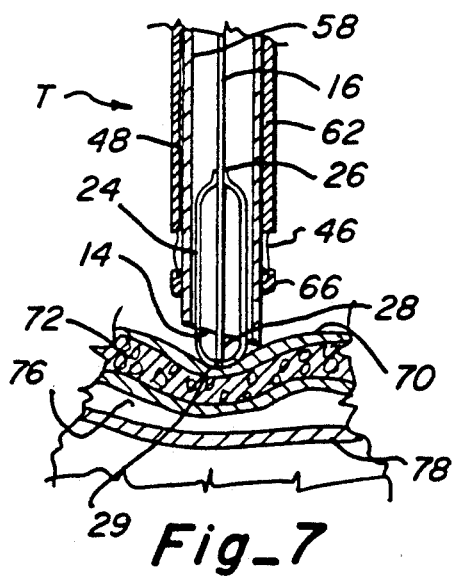
Fig_7
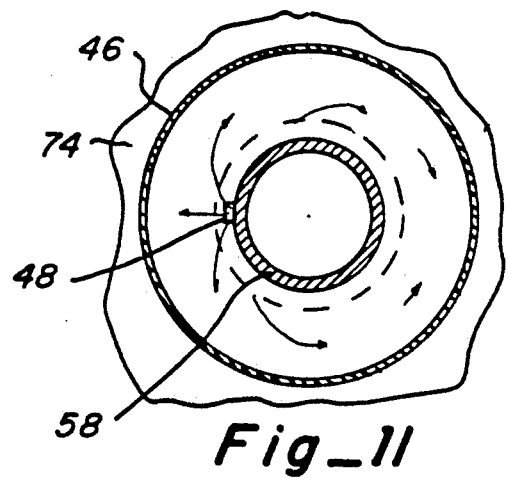
Fig_11
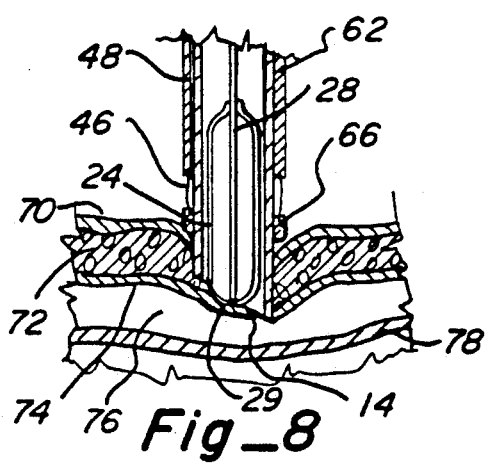
Fig_8
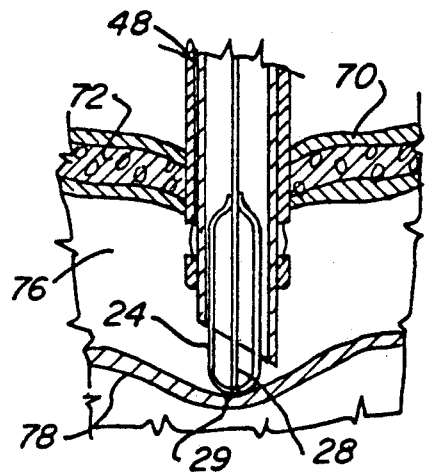
Fig_9
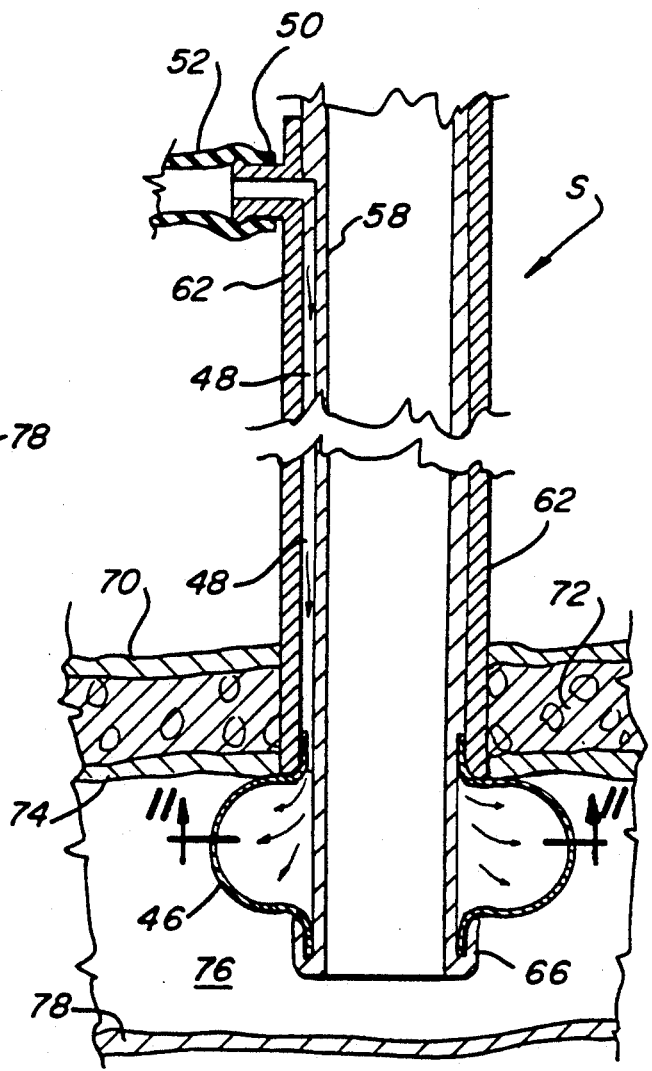
Fig_10

TROCHAR SYSTEM FOR LAPAROSCOPY

This is a continuation of U.S. patent application Ser. No. 896,461 filed Jun. 8, 1992 which is a continuation of U.S. patent application Ser. No. 625,413 filed Dec. 11, 1990.

TECHNICAL FIELD

This invention relates to a trochar system or insufflation needle for laparoscopy and more particularly to one which is inexpensive to manufacture and which is constructed, in one form of the invention, to minimize accidental dislodgement after placement in the patient.

BACKGROUND ART

The Veress Needle was originally designed for insertion into the chest to collapse a lung in treatment of tuberculosis. Later, when laparoscopy was first introduced to allow surgeons to look into the peritoneal cavity, the needle found new usage in filling the abdominal cavity with carbon dioxide. The Veress Needle comprises an outer cannula which has a needle point for easy penetration of the skin and underlying structures in the abdominal wall. The outer cannula expands into a relatively long needle hub which is used to house a spring mechanism for retraction of an inner cannula. This inner cannula includes a hollow tube having an enclosed end which is rounded to help avoid injury of the intra-abdominal structures. There is a side hole spaced above the distal end of the inner cannula to allow flow of carbon dioxide gas. Thus, when the needle point is pushed through the skin and other structures of the abdominal wall, the inner cannula is fully retracted within the inner cannula to allow easy penetration all the way through the abdominal wall. After the abdominal wall is penetrated, the inner, rounded tip, snaps forwardly into the space of the abdominal cavity and pushes underlying movable structures out of the way, such as large or small bowel or intestine, omentum or liver. The gas is then delivered to the abdominal cavity via a gas delivery system which is connected to the upper hub or valve section of the Veress Needle by a long plastic delivery tube. This gas creates a space or work area within the abdomen whereby good visualization is provided through a separate laparoscope. Any definitive surgical procedures, such as tubal ligations must generally be done through a separate opening, unless an operative laparoscope is utilized.

Although the Veress Needle has been a very useful instrument for about fifty years, it has certain drawbacks. It is a complex design and therefore expensive to manufacture. Because of its construction and small parts, the parts can be lost during cleaning and it is virtually impossible to clean the side hole adjacent the blunt tip of the inner cannula, resulting in small pieces of tissue and tissue fluid being transferred from one patient to the next. Also, after repeated use, the point becomes dull. Furthermore, the needle can be dislodged if left in place during an entire operative procedure and must be reinserted. Also, because of the rigid construction, the sharp end may be driven into the abdomen and cause damage to intra-abdominal contents such as the bowel, liver or major blood vessels if accidentally bumped by the surgeon. Furthermore, the Veress Needle can only be used for gas delivery and is not usable for a port hole for introduction of a laparoscope, operating instruments, cautery devices, laser fiber or other devices. If these devices are used they must be introduced through an additional trochar which creates an additional incision in the patient.

The most pertinent art is my U.S. Pat. No. 4,869,717 for "Gas Insufflation Needle With Instrument Port". A disposable trochar is provided which has a removable rod and needle portion within an outer sheath. The rod has a blunt end and is retractable during insertion so that the needle edge cuts through the abdominal wall. Once passing through the wall the rod extends so as to protect the bowel from the sharp needle. A gas port is provided for introducing gas through the rod and out a side passageway near the blunt end. After the abdomen is extended, the rod and needle can be removed as a unit from the sheath and thrown away and a suitable instrument introduced through an instrument port having a separate diaphragm. The gas can continue to be introduced around the instrument and into the abdomen while the instrument is in place. After the required medical procedures are completed, the instrument is removed. Then the sheath and associated parts are removed and thrown away. Other instruments have been devised which comprise concentric cannulas for various procedures. Among these instruments are the following:

U.S. Pat. No. 1,527,291 to Zorraquin shows a surgical needle which has a spring urged blunt rod within it to permit exploration of internal body cavities without perforating the wall of the cavity being explored.

U.S. Pat. No. 2,630,803 to Baren shows a pneumothoracic needle with spring-loaded inner blunt needle and an outer sharp cannula. The inner blunt needle is hollow and is removable without extracting the cannula from the chest wall.

U.S. Pat. No. 3,840,008 to Noiles discloses a hypodermic needle for safely injecting fluid into nerve and vessel crowded areas of a patient. The needle has a pointed hollow piercing member slidably mounted about a fluid delivery tube. The delivery tube has a blunt nose with at least one fluid opening near its blunt end, the other end being connected to a conventional syringe. The hollow piercing member is connected to the delivery tube by a finger-operated collapsible bar. The bar is provided with a centrally located groove to facilitate collapse at the moment the operator removes the force of his finger. The blunt nose delivery tube is then free to penetrate the tissue of the patient without endangering nerve or vessel.

U.S. Pat. No. 3,982,533 to Wiest discloses a device for introducing limited quantities of carbon dioxide into the human body for operational purposes, particularly laparoscopy. It includes a control device for delivering the carbon dioxide, a connecting nipple on the control device for connecting a flexible tubing to a Veress Needle introduceable into the body and a pressure gage for indicating the pressure present in the body cavity. A second connection nipple is provided on the control device and connected by a nipple to the pressure gage. The second connection nipple is connected by a further flexible tubing either to a dual Veress Needle or to a second single Veress Needle, so that the pressure gage is directly connected with the body cavity rather than through the operative Veress Needle.

U.S. Pat. No. 4,096,860 to McLaughlin discloses an encatheter incorporating a plastic insertion conduit placed into a blood vessel with a needle. The structure includes an elastomeric sealing flapper or one-way valve that allows insertion of a syringe needle.

U.S. Pat. No. 4,424,833 to Spector et al. describes a molded self-sealing gasket assembly through which, for instance, a catheter may be inserted and removed.

U.S. Pat. No. 4,535,773 to Yoon shows a safety puncturing instrument and method using a shielding mechanism that is biased to protrude from the distal end of the instrument to shield its sharp, penetrating point after the point has penetrated.

U.S. Pat. No. 4,769,018 to Wilson discloses a surgical cannula assembly for receiving and guiding a surgical instrument which has an instrument portion insertable through the cannula assembly and includes two selectively interconnectable and separate cannula sub-assemblies.

U.S. Pat. No. 4,808,168 to Waring discloses a single-use Veress-type pneumoneedle that has a flanged handle and a fixed valve sub-assembly that permits the pneumoneedle to be gripped like a syringe when it is being inserted. The stylet body is either a solid rod or a hollow tube. Insufflating gas is carried into the abdominal cavity through the lumen of the needle when the stylet is a solid rod or through the stylet lumen when the stylet is a hollow tube.

French Patent No. 2,308,346 to Storz discloses a probe for insertion of surgical instruments or insufflation tubes in the cavities of a body. It has a probe sleeve in which the instrument or tube is guided axially and which is enclosed by a tubular casing so as to form an air passage around it with air entry ports at the end.

DISCLOSURE OF THE INVENTION

In accordance with this invention a generally disposable trochar for use as a gas insufflation needle is provided for insertion through the abdominal wall of a patient and into a body cavity. It has an outer sheath with a tubular body, a distal open end and a proximate open end. The distal end optionally may have means which is expandable after the trochar has been inserted into the body cavity to minimize dislocation of the outer sheath during use. This optional feature generally will be used in larger diameter devices and omitted in smaller diameter devices. A cannula is removably received within the sheath which has a sharp distal end extendable beyond the distal end of the sheath and an enlarged head at the proximate end of the cannula. The head has a flat land which is engageable with the proximate end of the sheath to limit the extension of the distal end of the cannula beyond the distal end of the sheath. A rod is mounted within the cannula for longitudinal movement between a retracted position and an extended position. A blunt member is provided at the distal end of the rod extending beyond the sharp distal end of the cannula when in extended position. Resilient means is attached to the rod urging it toward the extended position.

More particularly, the head can be provided with a cannula which has a coil spring therein as the resilient means, the coil spring being connected to and formed integrally with the proximate end of the rod. The rod can be made up of a pair of wires, the first wire constituting an integral extension of the rod which is bent back upon itself and has an end attached to the side of the rod to form a first loop which moves with the rod between the retracted and extended position. In the smaller diameter devices, this single loop will be sufficient. In larger diameter devices, a second wire is bent into a second loop and positioned transversely of the first loop and has opposite ends attached to the side of the rod adjacent the first wire end. The single loop hairpin configuration or the double loop eggbeater type configuration each serve to minimize the chance of the sharp distal end of the cannula coming in contact with the bowel or other body surfaces which are to be protected. If desired, the wire can be formed in a flat configuration at the loops to provide a larger contact surface with the bowel.

The extendable means comprises an inflatable bladder adjacent the distal end of the outer sheath and an inflation tube which is in fluid communication with the bladder and runs longitudinally of the sheath. The inflation tube has a proximate end outside of the proximate end of the sheath. A check valve is connected to the proximate end of the tube for controlling flow of fluid to the bladder.

In addition, an inlet port is provided in the side of the sheath adjacent the proximate end of the sheath for supplying $CO_2$ gas to the body cavity. A spring biased pivotal closure is mounted within the sheath adjacent the proximate end thereof which is normally urged to a closed position to seal the proximate open end and minimize the escape of $CO_2$ gas. It is movable to an open position upon insertion of the cannula or other surgical instrument through the proximate end of the sheath.

A novel method is provided with the above apparatus which includes the steps of pressing the sharpened end of the cannula against the skin of the abdomen to cause the rod to be retracted. The sharpened end of the cannula is then thrust through the abdominal wall into the space between the peritoneum and the bowel to position the distal end of the sheath through the opening formed by the cannula. The rod then is extended beyond the sharpened end into the space between the peritoneum and the bowel. The annulus is inflated to hold the sheath in place within the opening. Gas is then introduced into the sheath to inflate the abdomen. The cannula and rod are then removed from the sheath. The spring closure is closed upon removal of the cannula and rod and then reopened upon introducing an instrument through the sheath into the abdomen space. Additional gas can be introduced through the sheath while an instrument is in place. Finally, the instrument can be removed from the sheath and the annulus deflated and the sheath removed from the opening to complete the operative process.

The devices just described are of simple construction, with few parts, thereby substantially reducing cost of parts and assembly. Thus, the device can be disposable, thereby eliminating any possibility of transferring contamination from one patient to another.

Additional advantages of this invention will become apparent from the description which follows, taken in conjunction with the accompanying drawings.

BRIEF DESCRIPTION OF THE DRAWINGS

FIG. 1 is an exploded view of a trochar system constructed in accordance with this invention;

FIG. 2 is an enlarged vertical section, taken along line 2—2 of FIG. 1, showing details of the insufflation needle;

FIG. 3 is a bottom plan view, taken along line 3—3 of FIG. 2;

FIG. 4 is an enlarged vertical section, taken along line 4—4 of FIG. 1, showing details of the outer sheath;

FIG. 5 is a horizontal section, taken along line 5—5, showing details of the inflatable annulus;

FIG. 6 is a side elevation, with parts broken away, of the trochar system in assembled position;

FIG. 7 is a diagrammatical view of a portion of the abdomen showing the positioning of the insufflation needle prior to insertion;

FIG. 8 is a view, similar to FIG. 7, but showing the beginning of the penetration of the needle through the abdominal wall;

FIG. 9 shows the insufflation needle in place within the abdominal cavity;

FIG. 10 shows the annulus of the outer sheath inflated to minimize unwanted displacement of the sheath; and FIG. 11 is a horizontal section, taken along line 11—11 of FIG. 10, showing the dispersion of air into the annulus.

BEST MODE FOR CARRYING OUT THE INVENTION

In accordance with this invention, as best seen in FIGS. 1 and 6, a needle or trochar T is provided which includes a cannula 10 having a head 12 at the proximate end and a sharp distal edge 14 for cutting through the abdominal wall of a patient. Within cannula 10 is a vertically slidable rod 16, as best seen in FIG. 2. Head 12 has a recess or cavity 18 whose diameter is greater than that of cannula 10. A coil spring 20 is provided in cavity 18 within head 12 and has a lower end integrally formed or attached to rod 16. Coil spring 20 also has a diameter which is greater than that of cannula 10 and may rest on flange 22 at the proximate end of cannula 10. The lower end of wire 16 is bent back upon itself to form a loop 24 and has an end 26 which is connected to the side of rod 16, as by soldering. In the smaller diameter devices this single loop will be sufficient. In larger diameter devices a second wire is formed into a loop 28 having its ends also soldered to the side of rod 16 adjacent end 26. This eggbeater type construction forms a blunt end 29. This blunt end or that formed by single loop 24 minimized the chance that the sharp edge 14 of the cannula 10 will come in contact with and perforate the bowel or other body surface. The wire can be formed in a flat rectangular configuration to provide a flat bearing surface.

The trochar T may be received within a sheath S having an elongated body 30 with a connector 32 at the proximate end thereof. As best seen in FIG. 4, the connector has a Leur lock 34 at the upper end thereof for attachment to a suitable medical instrument. The connector also includes an inlet port 36 in one side thereof through which a gas, such as $CO_2$ may be introduced to inflate the abdomen of the patient after the device is inserted through the abdominal wall, as will be described below. The connector 32 also has a door 38 which normally closes off passageway 40 to prevent escape of the $CO_2$ gas. The door 38 is urged toward closed position by coil spring 42 and seals against a gasket 44. When the trochar or other instrument is placed inside sheath S, the door 38 will be pushed downwardly to the position shown in dotted lines. Conveniently, land 45 of head 12 engages Leur lock 34 to limit the projection of blunt end 29 beyond the distal end of sheath 30.

The lower end of body 30 optionally has an annular inflated bladder 46 which is in fluid communication by means of passageway 48 to an inlet 50 located near the proximate end of body 30. This inlet is connected by means of a hose 52 to a supply valve 54 in turn connected to a supply hose 56. It will be understood that annular bladder 46 could be replaced with any expandable or extendable device which is operable by air pressure. Also it is conceivable that a low voltage electrical circuit could be used in place of the pneumatic device shown to activate an expandable member to minimize the displacement of sheath S once it is inserted into a body cavity. The body 30 is illustrated as having an inner sleeve 58 with a flange 60 at its upper end which is received within the lower portion of connector 32. Body 30 also has an outer sleeve 62 whose distal end grips the edges of bladder 46. The distal end of bladder 46 is received in a recess 64 in rib 66 at the distal end of inner sleeve 58. In smaller devices the bladder 46 may be omitted, but is particularly desirable with large diameter devices.

In order to accommodate different sizes of instruments and minimize the escape of air through passageway 40, an insert 68 can be provided to reduce the effective size of passageway 40 so as to accommodate a smaller instrument. Inserts can be provided of different sizes and they can be color coded, if desired, so that the size of the insert will be readily apparent to the user.

The use of the insufflation needle of this invention is best illustrated in FIGS. 7-11. To insert the insufflation needle, the blunt end 29, formed by a single loop 24 or double loops 24 and 28, is pressed against the surface of skin 70 and the needle is thrust downwardly against the skin. This motion causes the rod 16 to be retracted into cannula or needle 10 against the force of spring 20 which is compressed within recess 18. The exposed sharp edge 14 of cannula 10 pierces the skin 70 and fat 72 as shown in FIG. 8. The needle then passes through the peritoneum 74 into an air space 76 formed between the peritoneum and bowel 78. When the needle enters the air space 76, there is no longer any pressure against blunt end 29 of rod 16 so that spring 20 expands to extend rod 16 whereby loops 24 and 28 protect the bowel from the sharp edge 14 of cannula 10. A gas, such as carbon dioxide, can be introduced through inlet 36 and pass through inner sleeve 58 and the space between inner sleeve 58 and cannula 10 into the air space. The gas may be introduced at sufficient pressure to distend the abdominal cavity to a considerable extent.

In order to maintain sheath S in position within the opening formed through the abdominal wall, a gas such as compressed air, may be introduced through inlet hose 52 and inlet 50 which is transmitted through passageway 48 to bladder 46 causing the bladder to be extended, as best shown in FIG. 10. This pressure may be maintained as long as the sheath is to be positioned in the body cavity.

After this is done, the trochar T can be withdrawn which will allow door 38 to close under the influence of spring 42 against gasket 44 to prevent escape of the $CO_2$ gas being introduced through inlet 36. An instrument can be inserted through the passageway which was previously occupied by the trochar. As previously described, suitable inserts, such as insert 68, can be first inserted in passageway 40 to reduce the size of the passageway to one appropriate for the particular instrument being introduced which will not only more positively fix the position of the instrument but will minimize the escape the gas around the instrument when door 38 is opened upon insertion of the instrument.

After the operative procedure is completed, the instrument can be withdrawn, the pressure can be relieved to bladder 46 so that it collapses and the sheath can be removed.

From the foregoing, the advantages of this invention are readily apparent. A disposable insufflation needle has been provided which can be used to introduce gas into an abdominal cavity to extend the same while at the same time introducing a suitable instrument, all of this being accomplished through a single incision made by a trochar. The insufflation needle is of simple construction which includes a rod having an integral spring at one end and an eggbeater shaped integral distal end within a needle which is removable from an outer sheath after the device is inserted in the abdomen. During insertion, the rod is retracted and needle inserted through the skin whereupon the rod extends under the influence of the spring bias so that the distal end protects the bowel or other organs from the sharp edge of the needle. The loops at the distal end can be formed from rectangular wire to provide a larger bearing surface against the bowel or other organs. Then the rod and needle can be removed together and a bladder or other expandable device can be extended to minimize the possibility of the sheath being inadvertently dislodged from the opening through the skin. Other instrumentation can be introduced through the sheath for running appropriate procedures and/or operations on the patient. At the same time, gas can be introduced through the sheath around the instrument to distend the abdomen to a sufficient extent to allow the procedures to be conducted.

This invention has been described in detail with reference to particular embodiments thereof, but it will be understood that various other modifications can be effected within the spirit and scope of this invention.

I claim:

1. A disposable trochar in the form of a gas insufflation needle for insertion through an abdominal wall into a body cavity for the simultaneous introduction of $CO_2$ gas and medical instruments into the body cavity for diagnosis and/or treatment, said trochar comprising:

a rigid cannula having a first outside diameter, a cutting edge of the distal end thereof for cutting through the abdominal wall and an enlarged head at the proximate end having a cavity therein in communication with said cannula;

a coil spring mounted in said cavity;

a rod mounted for longitudinal movement between a retracted position and an extended position within said cannula, said rod having a proximate end formed integrally with said spring and a distal end, said distal end being received within said distal end of said cannula when said rod is in said retracted position and extending beyond said distal end of said cannula when said rod is in said extended position and having an integral loop formed at said distal end of said rod;

an outer sheath having a tubular body with a proximate end and a distal end for receiving said cannula and having a length less than that of said cannula so that said distal end of said cannula extends beyond said distal end of said sheath, said outer sheath having a second inside diameter sufficiently greater than said first outside diameter of said cannula to allow passage of $CO_2$ gas therearound;

an inlet port through said sheath at said proximate end thereof to introduce $CO_2$ gas through said sheath and around said cannula to the body cavity to expand it with said cannula in place within said sheath; and a spring biased closure within said sheath between said inlet port and said proximate end of said sheath to close said proximate end thereof when said cannula is withdrawn from said sheath to minimize escape of the $CO_2$ gas therethrough.

2. Apparatus, as claimed in claim 1, further including:
   an extendable member adjacent said distal end of said sheath for holding said distal end of said sheath in place in the body cavity.

3. Apparatus, as claimed in claim 1, wherein:
   said distal end of said rod is formed as two wire loops which lie in substantially perpendicular planes.

4. The apparatus as in claim 1, further including:
   a cylindrical insert selectively positioned in said proximate end of said central passageway having an inside diameter to size said proximate end of said central passageway to receive an instrument of smaller diameter than said cannula and having an outside diameter substantially the same as said inside diameter of said insert.

5. A disposable trochar in the form of a gas insufflation needle for insertion through an abdominal wall into a body cavity for the simultaneous introduction of $CO_2$ gas and medical instruments into the body cavity for diagnosis and/or treatment, said trochar comprising:

a rigid cannula having a first outside diameter, a cutting edge on the distal end thereof for cutting through the abdominal wall and an enlarged head at the proximate end having a cavity therein in communication with said cannula;

a coil spring mounted in said cavity;

a rod mounted for longitudinal movement between a retracted position and an extended position within said cannula, said rod having a proximate end formed integrally with said spring and a blunt distal end, said blunt distal end being received within said distal end of said cannula when said rod is in said retracted position and extending beyond said distal end of said cannula when said rod is in said extended position;

an outer sheath having a tubular body with a proximate end and a distal end for receiving said cannula and having a length less than that of said cannula so that said distal end of said cannula extends beyond said distal end of said sheath, said outer sheath having a second inside diameter sufficiently greater than said first outside diameter of said cannula to allow passage of $CO_2$ gas therearound;

an inlet port through said sheath at said proximate end thereof to introduce $CO_2$ gas through said sheath and around said cannula to the body cavity to expand it with said cannula in place within said sheath; and a spring biased closure within said sheath between said inlet port and said proximate end of said sheath to close said proximate end thereof when said cannula is withdrawn form said sheath to minimize escape of the $CO_2$ gas therethrough.

6. Apparatus, as claimed in claim 5, further including:
   an extendable member adjacent said distal end of said sheath for holding said distal end of said sheath in place in the body cavity.

7. The apparatus as in claim 5, further including a cylindrical insert selectively positioned in said proximate end of said central passageway having an inside diameter to size said proximate end of said central passageway to receive an instrument of smaller diameter than said cannula and having an outside diameter substantially the same as said inside diameter of said insert.

* * * * *